United States Patent [19]

Trojer et al.

[11] 4,120,730

[45] Oct. 17, 1978

[54] BIOCOMPATIBLE CERAMIC GLASS

[75] Inventors: Felix Trojer, Grand Lancy, Switzerland; Grahame Paul O'Connor, West-Wickham, England; Helmut Tannenberger, Geneva, Switzerland

[73] Assignee: Battelle Memorial Institute, Carouge, Geneva, Switzerland

[21] Appl. No.: 659,019

[22] Filed: Feb. 18, 1976

[30] Foreign Application Priority Data

Feb. 20, 1975 [CH] Switzerland .................... 2132/75

[51] Int. Cl.² .......................... C03C 3/22; C03C 3/04
[52] U.S. Cl. ........................................... 106/39.6
[58] Field of Search ................ 106/52, 39.6; 3/1.9

[56] References Cited

U.S. PATENT DOCUMENTS

| 3,241,935 | 3/1966 | Stookey | 106/39.6 |
| 3,919,723 | 11/1975 | Heimke et al. | 3/1.9 |
| 3,922,155 | 11/1975 | Broemer et al. | 106/39.6 |
| 3,929,971 | 12/1975 | Roy | 3/1.9 |

*Primary Examiner*—O. R. Vertiz
*Assistant Examiner*—Mark Bell
*Attorney, Agent, or Firm*—Karl F. Ross

[57] ABSTRACT

A biocompatible glass ceramic consisting of a vitreous matrix containing vitreous inclusions in which are dispersed crystals of a compound, isomorphous with hydroxyapatite, of at least the following elements: calcium, a lanthanide or yttrium, silicon, phosphorus and oxygen, these inclusions being surrounded by crystals of at least one compound belonging to the group consisting of $Na_2Ca_2Si_3O_9$ and $Ca_3(PO_4)_2 \cdot 2\, Ca_2SiO_4$, can be used to construct artificial bone segments etc in bone surgery and bonds firmly with the new bone tissue without causing inflammation.

5 Claims, No Drawings

BIOCOMPATIBLE CERAMIC GLASS

This invention relates to biocompatible glass ceramic in bone surgery.

It has already been proposed to use a biocompatible ceramic glass in constructing artificial bone segments. In particular, a glass ceramic and the results of tests on grafting this glass into bone tissues of living rats have been described in the following publication: C. A. Beckham, T. K. Greenlee, Jr. and A. R. Crebo, Calc. Tiss. Res. 8, pages 165–171 (1971).

In contrast, aluminate-based porous ceramic materials and their use in constructing artificial bone segments have been described in the following publications: Hulbert, S. F., Klawitter, J. J., Talbert, C. D. and Fitts, C. T.: "Materials of construction for artificial bone segments" in "Research in dental and medical materials", By E. Korostoff, New York: Plenum Press 1969; Smith, L: Ceramic-plastic material as a bone substrate. Arch. Surg. 87, 137–145 (1963).

The reason for using these materials in the construction of artificial bone segments is to avoid the undesirable reactions in the body which are produced when other materials such as metals and synthetic resins are used for this purpose, while at the same time obtaining a rigid durable joint between the bone and the articial segment.

The reason for the absence of reaction in the case of the above-mentioned aluminate-based porous ceramic materials, and glass ceramic is probably because of the particularly inert chemical nature of these materials, which may be termed "biocompatible".

The rigidity and durability of the joint between the bone and artificial segment in the case of porous ceramic materials results from a bone growth in the pores of these materials, and in the case of glass ceramic results from the partial dissolution of the vitreous matrix and the growth of the bone, with a type of epitaxy between a crystalline bone phase having the composition and crystalline structure of hydroxyapatite, $Ca_{10}(PO_4)_6(OH)_2$, and a crystalline phase of the glass ceramic which has a chemical structure and crystallographic form akin to those of hydroxyapatite.

Experiments carried out on laboratory animals have however shown that whereas the biocompatibility of the porous ceramic materials and glass ceramic as described in the aforementioned publications is generally excellent, the same cannot be said for the strength of the joint obtained between the bone and an artificial segment constructed from one of these materials. In this respect, an examination of grafts in those materials which have been left for six weeks inside cavities formed in he tibia of living rats, these cavities corresponding very precisely in size to the grafts, has shown that even though periosteum formed around the grafts, there was no effective rigid joint between the actual bone tissue and the graft.

The object of the invention is to provide a biocompatible glass ceramic which may form an effective joint with the living bone tissue without giving rise to undesirable reactions by the organsim.

To this end, the glass ceramic according to the invention consists of a vitreous matrix containing vitreous inclusions in which are dispersed crystals of a compound, isomorphous with hydroxyapatite, of at least the following elements: calcium, a lanthanide (rare earth) or yttrium, silicon, phosphorus and oxygen, these inclusions being surrounded by crystals of at least one compound belonging to the group consisting of $Na_2Ca_2Si_3O_9$ and $Ca_3(PO_4)_2 \cdot 2\ Ca_2SiO_4$.

Thus, in comparison with the known discussed above, which is formed starting from a mixture containing only the following elements in addition to oxygen: silicon, phosphorus, calcium and sodium, the ceramic glass according to the present invention presents a different chemical composition, namely it contains at least one lanthanide or yttrium.

The presence of such an element in the glass ceramic according to the invention seems to play a determining role in obtaining the desired result. Grafting tests using samples of glass ceramic according to the invention in the bone tissue of living rats, tests identical with those mentioned heretofore in the case of known glass ceramic, have shown that a rigid joint is formed between these samples and the bone in consequence of the partial dissolution of the glass ceramic and the growth of bone tissue in the holes thus formed in the glass ceramic, this growth taking place with a type of epitaxy between the hydroxyapatite phase of the bone and the crystals in the glass ceramic which are isomorphous with the hydroxyapatite.

It therefore seems that the presence of lanthanide or yttrium in the proportions specified heretofore is necessary to really obtain the epitaxis growwth phenomenon mentioned in the aforementioned publication. Preferably lanthanum itself is used as the lanthanide, as it has the advantage over other rare earths or yttrium of having a certain absence of toxicity when incorporated in the glass ceramic according to the invention, the non-toxicity of the other available rare earths or of yttrium under the same conditions having not yet been proved. Naturally the glass of the present invention is limited to that containing non-toxic components.

In addition to the ingredients mentioned heretofore, the glass ceramic according to the invention may contain fluorine and/or a small proportion of alumina, this latter compound being present as a solid solution or in the form of at least one compound with other elements concerned in the composition of the glass.

The composition of the crystalline phase isomorphous with hydroxyapatite probably corresponds to the following formula:

$$Ca_{10-x}M_xSi_xP_{6-x}O_{25}$$

(where M is a lanthanide, especially lanthanum, or yttrium and x is an integer from 2 to 6) in the case of a glass ceramic which does not contain fluorine, while in the glass ceramic containing fluorine the composition probably corresponds to a formula which includes the following particular formula:

$Ca_6M_4Si_2P_4O_{24}F_2$ (where M is a lanthanide), especially $Ca_6La_4Si_2P_4O_{24}F_2$.

The process for manufacturing the glass ceramic according to the invention is characterized in that a mixture of mineral compounds comprising at least the following oxides: $SiO_2$, $Na_2O$; CaO; $P_2O_5$ and at least one oxide of a rare earth or yttrium, and/or compounds capable of generating these oxides by heating, this mixture having a molar composition lying within the following molar percentage limits:

$SiO_2$: 35 to 50
$Na_2O$: 20 to 30
CaO: 10 to 30
$P_2O_5$: 2.5 to 10
Rare earth or yttrium oxide: 3 to 10 is brought to a temperature at least equal to its melting point, the mixtuure is kept in the molten state for a time sufficient to obtain a homogeneous molten glass, the glass is solidified by cooling, and is subjected in its solid state to heat treatment which induces crystallization of said compound isomorphous with hydroxyapatite and crystallization of the at least one compound of formula $Na_2Ca_2Si_3O_9$ or $Ca_3(PO_4)_2.2\ Ca_2SiO_4$.

Besides the aforementioned ingredients, the initial mixture of compounds may incorporate at least one compound of fluorine, this compound being preferably sodium fluoride or calcium fluoride, in a quantity corresponding to a maximum proportion of these latter salts of 10 moles per cent and 5 moles per cent respectively. A suitable combination of several simple fluorine compounds, for example sodium and calcium fluorides mixed, could equally be used.

The use of a fluorine compound enables a glass ceramic to be obtained which, as the crystalline phase isomorphous with apatite, contains a combination containing the elements calcium, a lanthanide or yttrium, silicon, phosphorus, oxygen and fluorine, having a general formula of the type heretofore indicated. Such a glass ceramic has proved particularly suitable for forming a rigid durable liaison with the bone tissue.

In order to facilitate the heat treatment of the glass ceramic and to allow a product to be obtained with optimum mechanical, physical and chemical properties, and which is extremely suitable for forming a bond with living bone tissue, a quantity of alumina corresponding to a maximum proportion of the order of 5 moles per cent may be added to the initial mixture of compounds.

The chosen temperature at least equal to the melting point of the mixture is preferably between 1400° and 1600° C, and the time during which the glass is kept molten at this temperature is preferably 6 to 20 hours.

According to the speed of cooling of the glass, either a solid homogeneous vitreous mass is obtained (if the speed of cooling is so great that the viscosity of the mass reaches a value which prevents any separation of the vitreous phases before such a separation has had time to occur) or a two-phase glass is obtained consisting of a vitreous matrix containing vitreous inclusions.

Preferably the heat treatment is carried out in several operations, namely:
— annealing by heating to a temperature of 400° to 500° C for a time of 2 to 6 hours;
— nucleation of the crystalline compound amorphous with hydroxyapatite by heating to a temperature of 400° to 600° C for a time of 2 to 8 hours;
— growth of the crystalline compound isomorphous with hydroxyapatite by heating to a temperature of 800° to 1000° C for a time of 4 to 8 hours. During this latter operation, at least one other crystalline compound of formula $Ca_3(PO_4)_2.2\ Ca_2SiO_4$ or $Na_2SiO_4$ or $Na_2Ca_2Si_3O_9$ also crystallizes.

The heat treatment may equally be carried out in a single operation, namely heating for a temperature of 800° to 1000° C for a time of 15 to 60 minutes, if the homogeneous glass obtained in the first operation is reduced to a fine powder before subjecting it to heat treatment.

The glass ceramic according to the invention may be used in different ways for constructing artificial bone segments, the method of use being chosen according to the precise use for which the artificial segments are intended.

For example the glass ceramic may be used in the form of a piece consisting only of glass. Because of the good mechanical characteristics of the glass ceramic according to the invention, such a piece may be used in various ways, even where it is intended to replace a bone part which is subjected to relatively large mechanical stress. If an artificial segment is to be constructed to replace a bone or part of a bone which is subjected to particularly high forces, such as the leg bone, the glass ceramic may be used to form the exterior of an artificial segment the core of which consists of a piece of reinforcement in a material of high mechanical strength, for example an alloy such as Fe—Cr—Ni, Co—Cr—Mo etc.

The glass ceramic according to the invention may equally be used to obtain a solid permanent joint between a metal piece and a bone, for example in the case of an artificial collum femoris, grafted into a hip joint comprising a metal piece joined to the hip bone by the glass ceramic.

Numerous other applications of the glass ceramic according to the invention may be envisaged, particularly coating metal pieces such as the metal needles used to implant artificial teeth into the bone tissue of the jaw. In this way a rigid permanent fixing of the needle to the jaw is obtained, with the additional advantage of allowing the use of needles of a material more economical and more easy to work than the usual material used without a coating, namely tantalum.

Furthermore, the glass ceramic according to the invention may be used in the form of powder, especially as part of the composition of cements for making a solid joint between metal elements such as screws, plates etc. used for the temporary or permanent consolidation of the bone during surgical treatment of fractures, or it may be used as a surface coating for these elements.

EXAMPLE 1

A homogeneous glass is prepared by melting a mixture of mineral compounds of the following composition, expressed as percentage by weight and molar percentage:

|  | percentage by weight | molar percentage |
|---|---|---|
| $SiO_2$ | 30.57 | 45.0 |
| $Na_2CO_3$ | 27.07 | 22.5 |
| $CaO$ | 9.52 | 15.0 |
| $La_2O_3$ | 18.46 | 5.0 |
| $P_2O_5$ | 12.05 | 7.5 |
| $NaF$ | 2.38 | 5.0 | this melting operation being followed by maintaining the liquid state of 18 hours at 1450° C, and then cooling the homogeneous liquid thus obtained to 1000° C over 60 minutes so that it solidifies.

The homogeneous glass thus obtained is brought to 450° C and this temperature maintained for 5 hours. During this thermal treatment the separation of the glass into two amorphous phases is observed, one of which appears in the form of globular inclusions of a size of the order of 5,000 to 10,000 Angstroms dispersed regularly within the other phase, this latter thus forming a vitreous matrix. The two-phase glass thus obtained is brought to 800° C and kept at this temperature for 5 hours. Three different crystalline phases appear within the two vitreous phases. One of these phases is composed of crystals dispersed in the vitreous inclusions and having a crystalline structure of the hexagonal system, the crystalline parameter values being a = 9.617 A; c = 6.627 A. It therefore probably consists of a compound of fluorinated silico-apatite type, doped with lanthanum and phosphorous, i.e. a compound having a formula which includes the following particular formula:

$$Ca_6La_4Si_2P_4O_{24}F_2,$$

the other possible formulas being derived from this latter by varying the proportion of calcium, lanthanum, silicon, phosphorus and fluorine atoms within the allowable limits for maintaining the crystalline structure hexagonal. Such a compound is isomorphous with natural hydroxyapatite, $Ca_{10}(PO_4)_6(OH)_2$, which forms part of the living bone tissue.

The presumed formula stated heretofore is supported by the measurements made by N. F. Fedorov; I. F. Andreev; Sh. Yu. Azimov and T. P. Smorodina on a compound of formula $Ca_6Y_4(SiO_4)_4(PO_4)F_2$ formed in the $Ca_{10}(PO_4)_6F_2 - Ca_4Y_6(siO_4)_6F_2$ system (Inorganic Materials, volume 8, pages 284–286, 1972). According to these measurements, the compound has a hexagonal structure with the following crystalline parameters: a=9.33 A; c = 6.84 A.

The other two crystalline phases of the glass ceramic are in the form of crystals dispersed in the vitreous matrix and consisting respectively of a compound of formula $Na_2Ca_2Si_3O_9$ (structure: hexagonal; crystalline parameters: a = 10.48 A; c = 13.19 A) and a compound of formula $Ca_3(PO_4)_2$. 2 $Ca_2SiO_4$ (structure: hexagonal; crystalline parameters: a = 5.38 A; c = 7.10 A). The crystals of the first of these compounds have a size of the order of 1 to 5 microns and those of the second measure less than 1 micron.

Samples of this glass ceramic in the form of parallelpiped bars of length 3 mm and square cross-section with a side of 1 mm are grafted into cavities of corresponding dimensions formed in the tibia of one year old rats. The incisions are then closed and the wounds resulting from the operation are dressed. Six weeks after grafting, the wounds having completely healed without any inflammation, the rats are sacrificed and the grafts and the bond formed between the bone tissue and grafts are examined. New bone tissue is observed rigidly joined to the graft with partial dissolution of the glass ceramic. By chemical analysis using radioactive tracers, it is found that the new bone tissue contains a certain proportion of lanthanum originating from glass ceramic.

EXAMPLE 2

A glass ceramic is prepared in a manner similar to that described in example 1, but using as the initial mixture of compounds a mixture having the following weight and molar composition:

|  | percentage by weight | molar percentage |
|---|---|---|
| $SiO_2$ | 31.2 | 47.2 |
| $Na_2O$ | 27.5 | 23.6 |
| CaO | 9.8 | 15.7 |
| $La_2O_3$ | 19.1 | 5.3 |
| $P_2O_5$ | 12.4 | 8.0 |

Heat treatment is carried out at the temperature and for the times specified in example 1.

The structure of the glass ceramic obtained is similar to that of the glass ceramic prepared in accordance with example 1. However, the proportion of the compound isomorphous with hydroxyapatite is smaller and the size of the crystals of this compound are much smaller than in the case of the glass ceramic according to example 1, as shown by X-ray diffraction analysis.

Moreover, the formula of this compound corresponds in all probability to the following formula:

$$Ca_{10}La_xXi_xP_6O_{25}$$

where x is a number from 2 to 6.

Tests are carried out on sample grafts of this glass ceramic in the bones of living rats, in a manner identical with that described in example 1, with a result similar to the results of the tests described in that same example.

EXAMPLE 3

The procedure of example 1 is repeated, but using as the starting mixture of compounds a mixture containing 2.5 moles per cent of calcium fluoride $CaF_2$ instead of 5 moles per cent of sodium fluoride NaF.

The glass ceramic thus obtained is analogous to that described in example 1 and the results of tests on grafting this glass in bones of living rats are likewise similar to those of the tests described in example 1.

EXAMPLE 4

A glass ceramic is prepared starting from the same mixture of compounds as in example 1, but instead of carrying out the crystallisation heat treatment in two stages, the homogeneous glass obtained after fusion and rapid solidification of the mixture is reduced to a fine powder and this powder is brought to 800° C for 30 minutes.

The structure of the glass ceramic obtained is analogous with that of the glass ceramic prepared in accordance with example 1, and its ability to form a solid durable bond with the bone is the same as that of this latter glass ceramic.

EXAMPLE 5

The procedure of example 1 is repeated, but using the following starting mixture of compounds:

|  | percentage by weight | molar percentage |
|---|---|---|
| $SiO_2$ | 25.0 | 38.2 |
| $Al_2O_3$ | 5.5 | 4.9 |
| $Na_2CO_3$ | 27.0 | 23.3 |
| CaO | 9.5 | 15.5 |
| $La_2O_3$ | 18.5 | 5.2 |
| $P_2O_5$ | 12.0 | 7.7 |
| NaF | 2.4 | 5.2 |

A glass ceramic is obtained with a structure and properties identical with those of the glass ceramic obtained in example 1.

EXAMPLE 6 (comparative)

A glass ceramic is prepared in a manner analogous with that described in example 1, but using the following starting mixture of compounds (composition given in molar percentage):
$SiO_2$: 45
CaO: 25
$Na_2O$: 25
$P_2O_5$: 5

For this purpose, the mixture is melted and kept in the liquid state at 1450° C for 18 hours, and is then solidified to form a vitreous homogeneous mass by cooling to 100° C over 60 minutes.

The homogeneous glass thus obtained is brought to 450° C for 4 hours and then to 800° C for 8 hours. A glass ceramic is obtained composed of two amorphous phases one of which is in the form of globular inclusions of a size of the order of 5,000 to 10,000 angstroms, dispersed within the other amorphous phase which forms a matrix. These vitreous globular inclusions contain crystals of a size of the order of 500 to 1,000 Angstroms, of a compound having a monoclinic crystalline structure with the following crystalline parameter values:

$$a = 5.48 \text{ A}; b = 6.78 \text{ A}; c = 9.28$$

and a beta angle of 94 degrees and 33 minutes. The formula of this compound derives from that of calcium silicate $Ca_2SiO_4$ by substituting a maximum of 30% of the silicon atoms by phosphorus atoms, and its structure is identical with that of the so-called "beta" form of calcium silicate. This compound is not isomorphous with the natural hydroxyapatite of living bone tissue.

The amorphous phase forming the matrix contains crystals of a size of the order of 10,000 A of the compound $Na_2Ca_2Si_3O_9$, of hexagonal crystalline structure and having the following crystalline parameter values: a = 10.48; C = 13.19, these crystals being dispersed in the matrix in the vicinity of the vitreous inclusions.

Grafting tests on this glass ceramic carried out under identical conditions to those described in example 1 have shown that an inflammatory effect is produced and, although periosteum is formed in the vicinity of the glass ceramic sample, there is no effective bond between the actual bone tissue and the ceramic glass sample, despite the fact that part of this latter is dissolved by the organism. In fact, this sample may be separated from the bone by simply pulling with tweezers, this being absolutely impossible in the case of a graft of glass ceramic obtained as described in example 1.

We claim:

1. A biocompatible glass ceramic consisting essentially of a $Na_2O$, $CaO$ and $SiO_2$ vitreous matrix containing vitreous inclusions in which are dispersed crystals of a compound isomorphous with hydroxyapatite and having the formula $Ca_{(10-x)}M_xSi_xP_{(6-x)}O_{24}F_2$, where $x$ is 2 to 6 and M is a lanthanide or yttrium, and crystals of $Na_2Ca_2Si_3O_9$ and $Ca_3(PO_4)_2.2Ca_2SiO_4$ in said matrix, said crystals being present in an effective amount to permit bonding of said glass ceramic to bone, the glass ceramic being prepared from a mixture having the following molar percentage limits:

$SiO_2$ = 35 to 50
$Na_2O$ = 20 to 30
$CaO$ = 10 to 30
$P_2O_5$ = 2.5 to 10
lanthanide or yttrium oxide = 3 to 10
alumina = up to 5
sodium fluoride = up to 10
calcium fluoride = up to 5.

2. The glass ceramic defined in claim 1 wherein said lanthanide is lanthanum.

3. The glass ceramic defined in claim 2 wherein said compound isomorphous with hydroxyapatite is a compound of the formula $$Ca_{10-x}La_xSi_xP_{6-x}O_{25}.$$

4. The glass ceramic defined in claim 1 wherein said compound isomorphous with hydroxyapatite is a compound of the formula $$Ca_6La_4Si_2P_4O_{24}F_2.$$

5. The glass ceramic defined in claim 1 wherein said crystals isomorphous with hydroxyapatite include said lanthanide or yttrium in a nontoxic quantity but sufficient to permit partial dissolution of the glass ceramic to form holes and allow growth of bone tissue in these holes whereby the lanthanide or yttrium is incorporated in the bone tissue thus grown in the holes whereby epitaxy exists between the hydroxyapatite phase of the bone and crystals of the ceramic glass isomorphous with the hydroxyapatite.

* * * * *